US008894881B2

(12) United States Patent
Hamel et al.

(10) Patent No.: US 8,894,881 B2
(45) Date of Patent: Nov. 25, 2014

(54) 1,8-NAPHTHALIMIDE DERIVATIVES AS SCINTILLATION AGENTS, IN PARTICULAR FOR DISCRIMINATING BETWEEN FAST NEUTRONS AND GAMMA RAYS

(75) Inventors: Matthieu Hamel, Cherbourg (FR); Stéphane Normand, Mantes la Jolie (FR); Vesna Simic, Chaville (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 656 days.

(21) Appl. No.: 12/864,777

(22) PCT Filed: Jan. 27, 2009

(86) PCT No.: PCT/EP2009/050865
§ 371 (c)(1),
(2), (4) Date: Jul. 27, 2010

(87) PCT Pub. No.: WO2009/095376
PCT Pub. Date: Aug. 6, 2009

(65) Prior Publication Data
US 2010/0314556 A1 Dec. 16, 2010

(30) Foreign Application Priority Data
Jan. 31, 2008 (FR) ...................................... 08 50611

(51) Int. Cl.
*C09K 11/02* (2006.01)
*C09K 11/06* (2006.01)
*C07D 221/14* (2006.01)

(52) U.S. Cl.
CPC .................................. *C07D 221/14* (2013.01)
USPC .................................. 252/301.36; 252/301.17

(58) Field of Classification Search
USPC .................... 252/301.17, 301.36; 250/370.11, 250/370.12
See application file for complete search history.

(56) References Cited

U.S. PATENT DOCUMENTS

| 5,314,740 | A | * | 5/1994 | Ishii et al. ..................... 428/209 |
| 6,288,232 | B2 | * | 9/2001 | Shershukov et al. ........... 546/52 |
| 2002/0198385 | A1 | * | 12/2002 | Lewis et al. ................... 546/122 |
| 2007/0189987 | A1 | * | 8/2007 | Luukas ............................ 424/59 |
| 2008/0241416 | A1 | * | 10/2008 | Shimohara et al. ........... 427/511 |

FOREIGN PATENT DOCUMENTS

| BE | 612 955 A1 | 5/1962 |
| GB | 1003083 | 9/1965 |
| WO | WO 2007074461 A1 * | 7/2007 |

OTHER PUBLICATIONS

Le Barny et al., 'Detection of nitroaromatic compounds based on photoluminescent side chain polymers', 2005, Proc. of SPIE, vol. 5990, pp. 59900S-1 to 59900S-8.*
Vasil'chenko et al., 'New Liquid Scintillators for Detectors Based on Capillary Fibers', 1997, Instruments and Experimental Techniques, vol. 40, pp. 175-185.*
EIC search report (Sep. 23, 2013).*
Hamel et al., "Fluorescent 1,8-naphthalimides—containing polymers as plastic scintillators. An attempt for neutron-gamma discrimination", Sep. 30, 2008, Reactive & Functional Polymers, vol. 68, pp. 1671-1681.*
Grabchev et al., "1,8-Naphthalimides as Blue Emitting Fluorophores for Polymer Materials", Macromol. Mater. Eng., 2002, vol. 287, pp. 904-908.*
Magalhaes et al., "Solvent effect on the photophysical properties of 4-phenoxy-N-methyl-1,8-naphthalimide", 2006, Journal of Photochemistry and Photobiology, vol. 183, pp. 165-170.*
Vasil'Chenko et al., "New Liquid Scintillators for Detectors Based on Capillary Fibers", Instruments and Experimental Techniques, vol. 40, No. 2, 1997, pp. 175-185, XP008097769.
Beresnev et al., "Spectrum-Shifting Lightguides for Large Scintillation and Cerenkov Detectors", Journal Atomic Energy, vol. 64, No. 3, 1988, pp. 268-274, XP008097768.
Vasil'Chenko et al., "New Results on Radiation Damage Studies of Plastic Scintillators", Nuclear Instruments and Methods in Physics Research, Section A: Accelerators, Spectrometers, Detectors, and Associated Equipment, vol. 369 (1996), pp. 55-61, XP004003164.
Britvich et al., "Investigation of Radiation Resistance of Polystyrene-Based Scintillators", Instruments and Experimental Techniques, vol. 36, No. 1, 1993, pp. 74-80, XP008097800.
Britvich et al., "Radiation Damage Studies on Polystyrene-based Scintillators", Nuclear Instruments and Methods in Physics Research, Section A: Accelerators, Spectrometers, Detectors, and Associated Equipment, vol. 326 (1993), pp. 483-488, XP002501673.
Kesanli et al., "Highly Efficient Solid-State Neutron Scintillators Based on Hybrid Sol-Gel Nanocomposite Materials," Applied Physics Letters, No. 89, pp. 214104-1 to 3, 2006.
Normand et al., "Discrimination Methods Between Neutron and Gamma Rays for Boron Loaded Plastic Scintillators," Nuclear Instruments & Methods in Physics Research, Section A, No. 484, pp. 342-350, 2002.
Barnik et al., "New Scintillating Media Based on Liquid Crystals for Particle Detectors," Nuclear Instruments & Methods in Physics Research, Section A, No. 449, pp. 537-545, 2000.
Moszynski et al., "Study of n-Y Discrimination with NE213 and BC501A Liquid Scintillators of Different Size," Nuclear Instruments & Methods in Physics Research, Section A, No. 350, pp. 226-234, 1994.

* cited by examiner

*Primary Examiner* — Carol M Koslow
*Assistant Examiner* — Lynne Edmondson
(74) *Attorney, Agent, or Firm* — Miles & Stockbridge P.C.

(57) ABSTRACT

The invention relates to the use of 1,8-naphthalimide derivatives and of their salts as scintillation agents and more specifically as agents for discriminating between fast neutrons and gamma rays.
It also relates to liquid scintillators comprising these scintillation agents in solution in a solvent and to novel 1,8-naphthalimide derivates of use as scintillation agents, in particular for discriminating between fast neutrons and gamma rays.
Applications: all the fields of use of scintillators and in particular industry, geophysics, fundamental physics, in particular nuclear physics, the safety of goods and people, protection from radiation of workers in the industrial, nuclear and medical sectors, medical imaging, and the like.

11 Claims, 5 Drawing Sheets

1,8-NAPHTHALIMIDE DERIVATIVES AS SCINTILLATION AGENTS, IN PARTICULAR FOR DISCRIMINATING BETWEEN FAST NEUTRONS AND GAMMA RAYS

TECHNICAL FIELD

The invention relates to the use of 1,8-naphthalimide derivatives as scintillation agents and more especially as agents for discriminating between fast neutrons and gamma rays.

It also relates to liquid scintillators comprising these scintillation agents in solution in a solvent and to novel 1,8-naphthalimide derivatives useful as scintillation agents, in particular for discriminating between fast neutrons and gamma rays.

The invention may have applications in all the fields where scintillators are used and in particular:

in the industrial field, for example for measuring physical parameters of components during manufacture, for the nondestructive inspection of materials, for monitoring radioactivity at the entrance and exit points of sensitive sites and for monitoring radioactive waste;

in the geophysical field, for example for evaluating the natural radioactivity of soil;

in the field of fundamental physics and in particular of nuclear physics;

in the field of the safety of goods and people, for example for the safety of critical infrastructures, checking moving merchandise (luggage, containers, vehicles, and the like) and the protection from radiation of workers in the industrial, nuclear and medical sectors; and in the field of medical imaging, which today represents one of the major fields of application of scintillators.

STATE OF THE PRIOR ART

The discrimination between fast neutrons and gamma rays, referred to more simply as "n/γ discrimination", is a method which makes it possible to distinguish the respective contributions of the interactions between the fast neutrons and the gamma rays with an organic scintillator.

This discrimination is rendered possible by the difference in shape of the signal produced by the scintillator during the radiation/material interaction.

There essentially exist two types of organic scintillators capable of discriminating between fast neutrons and gamma rays: organic solid scintillators and organic liquid scintillators.

Organic solid scintillators, which are manufactured from single crystals, for example of stilbene or of anthracene, generally make possible a good n/γ discrimination but the response depends on the angle of incidence of the particles. Furthermore, it is difficult to prepare organic solid scintillators of large size due to the high cost of manufacturing such scintillators.

Organic liquid scintillators, which themselves exhibit the advantage of high availability and of low manufacturing costs, even in large volumes, are composed of a complex mixture of several compounds.

This mixture generally comprises one or more organic solvents and at least two fluorophores: a primary fluorophore, the role of which is to convert electron energy into detectable light, and a secondary fluorophore, referred to as wavelength shifter, the role of which is to increase the emission wavelength of the scintillator in order to increase its efficiency of detection by photodetectors. Other compounds can optionally be added, such as surfactants, extractants or fillers, for specific usages of the scintillator.

Currently, the most widely used organic liquid scintillators are NE213, BC-501A from Bicron and Ultima Gold® AB from PerkinElmer.

Due to the complexity of their composition, these liquid scintillators have poor ageing properties and thus have to be packaged and stored under very strict conditions. Furthermore, they are extremely sensitive to gases and in particular to atmospheric oxygen capable of being dissolved therein, hence the need to frequently subject them to bubbling operations with inert gases (argon) in order to prevent phenomena of quenching (reduction in the fluorescence efficiency).

The Inventors thus set themselves the target of providing novel scintillation agents which, in addition to being capable of discriminating between neutrons and gamma rays, make it possible to produce organic solid or liquid scintillators which, generally, are devoid of the disadvantages exhibited by organic solid and liquid scintillators currently used to carry out such a discrimination.

In particular, the Inventors set themselves a target that these scintillation agents make it possible to produce liquid scintillators which, while having spectroscopic properties at least as advantageous as those of the liquid scintillators currently available, are sufficiently stable not to require any specific precautions for their packaging and their storage and are insensitive to the presence of dissolved gases in particular of dissolved oxygen.

They also set themselves the target that the synthesis of these scintillation agents and the preparation of solid or liquid scintillators starting from the latter be easy to carry out and involve only conventional handling operations used in organic chemistry.

ACCOUNT OF THE INVENTION

These aims and yet others are achieved by the invention which proposes, first, the use of a 1,8-naphthalimide derivative corresponding to the following general formula (I):

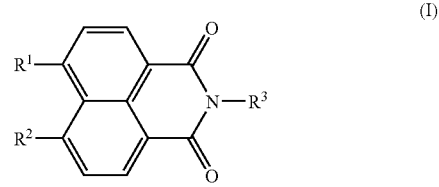

in which:
$R^1$ represents an electron-donating group;
$R^2$ represents a hydrogen atom or an electron-donating group identical to or different from $R^1$;
while
$R^3$ represents:
an acyl group, or
a saturated or unsaturated, linear or branched $C_1$ to $C_{20}$ hydrocarbon group which is optionally substituted, or
a saturated cyclic $C_3$ to $C_{10}$ hydrocarbon group which is optionally substituted, or
a saturated $C_3$ to $C_{10}$ heterocyclic group which is optionally substituted, or
an aryl or heteroaryl group which is optionally substituted;
or of one of its salts, as scintillation agent for discriminating between fast neutrons and gamma rays.

This is because the Inventors have found that, by substituting the 1,8-naphthalimide in the 4 position and/or in the 5 position with an electron-donating group, fluorescent compounds are obtained which exhibit spectroscopic properties such that it is possible to use them as scintillating agents and in particular as n/γ discrimination agents and to produce, with these compounds, organic liquid scintillators comprising just one fluorophore which are both stable over time and insensitive to dissolved gases.

In accordance with the invention, the electron-donating group or groups represented by $R^1$ and optionally $R^2$ are preferably chosen from:
- —OR' and —SR' groups, where R' represents a saturated or unsaturated, linear or branched $C_1$ to $C_{20}$ hydrocarbon group which is optionally substituted, or a saturated cyclic $C_3$ to $C_{10}$ hydrocarbon group which is optionally substituted, or an aryl or heteroaryl group which is optionally substituted; and
- —NR'R" groups, where R' has the same meaning as above while R" represents either a hydrogen atom, or a saturated or unsaturated, linear or branched $C_1$ to $C_{20}$ hydrocarbon group which is optionally substituted, or a saturated cyclic $C_3$ to $C_{10}$ hydrocarbon group which is optionally substituted, or an aryl or heteroaryl group which is optionally substituted.

In that which precedes and that which follows, the term "saturated or unsaturated, linear or branched $C_1$ to $C_{20}$ hydrocarbon group" is understood to mean any alkyl, alkenyl or alkynyl group which comprises at least 1 carbon atom but not more than 20 carbon atoms. Such a group is, for example, a methyl, ethyl, propyl, isopropyl, butyl, pentyl, neopentyl, hexyl, ethylenyl, propylenyl, butenyl, pentenyl, hexenyl, methylpentenyl, buta-1,3-dienyl, ethynyl, propynyl, butynyl, pentynyl or hexynyl group, and the like.

The term "saturated cyclic $C_3$ to $C_{10}$ hydrocarbon group" is understood to mean any group which is formed of a cycloalkyl or of several fused cycloalkyls and which comprises at least 3 carbon atoms but not more than 10 carbon atoms. Such a group is, for example, a cyclopropyl, cyclobutyl, cyclopentyl, cyclohexyl, bicyclohexyl or bicyclodecyl group, and the like.

The term "saturated $C_3$ to $C_{10}$ heterocyclic group" is understood to mean a monocyclic or polycyclic group which comprises one or more heteroatoms and which comprises at least 3 carbon atoms but not more than 10 carbon atoms. Such a group is, for example, a tetrahydrofuryl, tetrahydrothiophenyl, pyrrolidinyl, piperidyl or dioxanyl group, and the like.

The term "aryl group" is understood to mean a monocyclic or polycyclic group which satisfies the Hückel rule, that is to say which exhibits a number of delocalized π electrons equal to 4n+2 (with n=0, 1, 2, 3, . . . ), and the term "heteroaryl group" is understood to mean a group as just defined but which comprises one or more heteroatoms. Mention may be made, as examples of an aryl group capable of being used, of the cyclopentadienyl, phenyl, benzyl, biphenyl, pyrenyl, naphthyl, phenanthrenyl and anthracenyl groups while mention may be made, as examples of a heteroaryl group, of the furanyl, pyrrolyl, thiophenyl, oxazolyl, pyrazolyl, thiazolyl, imidazolyl, triazolyl, pyridinyl, pyranyl, quinolyl, pyrazinyl and pyrimidinyl groups.

Finally, the term "heteroatom" is understood to mean any atom other than carbon or hydrogen, such as, for example, an oxygen, sulphur, nitrogen, phosphorus or boron atom, it being understood, however, that the heteroatoms capable of being involved in rings are oxygen, nitrogen or sulphur atoms.

In accordance with the invention, it is preferable to use, as saturated cyclic $C_3$ to $C_{10}$ hydrocarbon groups and as saturated $C_3$ to $C_{10}$ heterocyclic groups, 5- or 6-membered monocyclic groups.

Similarly, it is preferable to use, as aryl or heteroaryl groups, 5 or 6-membered monocyclic groups or polycyclic groups not comprising more than 3 rings and better still no more than 2 rings, each comprising 5 or 6 ring members.

According to a first preferred arrangement of the invention, the 1,8-naphthalimide derivative exhibits an emission maximum wavelength of between 350 and 550 nm and better still between 380 and 470 nm.

This is the reason why preference reverts to the 1,8-naphthalimide derivatives corresponding to the general formula (I) in which $R^1$ represents an —OR' or —SR' group, where R' has the same meaning as above, while $R^2$ represents a hydrogen atom, the emission maximum wavelength of which lies in the vicinity of 420 nm.

Particularly preferably, $R^1$ represents a $C_1$ to $C_{20}$ and better still $C_1$ to $C_{10}$ alkoxy, alkenyloxy or alkylsulphanyl group, such as, for example, a methoxy, ethoxy, propoxy, butyloxy, pentoxy, octyloxy, vinyloxy, allyloxy, butenyloxy, hexenyloxy, methylsulphanyl, ethylsulphanyl, propylsulphanyl, butylsulphanyl, hexylsulphanyl or octylsulphanyl group.

According to another preferred arrangement of the invention, $R^3$ represents a group which is relatively bulky and hindering from a steric viewpoint, so as to optimize the signal/noise ratio. It is consequently preferable for $R^3$ to represent a cyclic group, typically an aryl or heteroaryl group, substituted in the 2 and 5 positions, with respect to the nitrogen atom of the naphthalimide ring system, by a branched $C_3$ to $C_6$ alkyl group, such as, for example, an isopropyl or t-butyl group. A cyclic group of this type is, for example, the di(t-butyl)phenyl group.

However, 1,8-naphthalimide derivatives having a simple linear alkyl chain, such as, for example, an n-butyl chain, for the $R^3$ radical have also proven to be advantageous.

According to yet another preferred arrangement of the invention, the 1,8-naphthalimide derivative is chosen from the derivatives 4, 5, 6, 7, 8, 9 and 12 represented below:

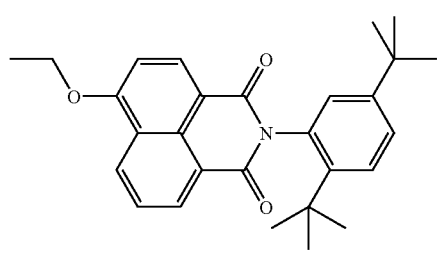

4

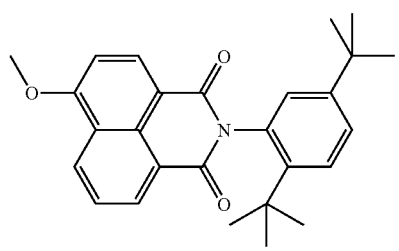

5

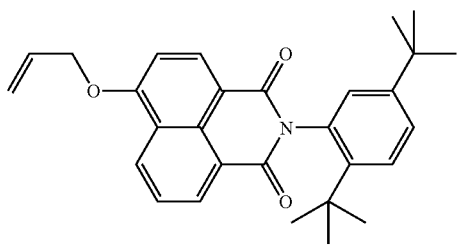

6

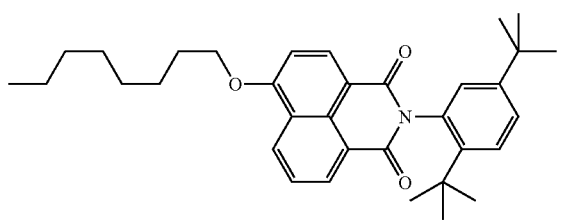

7

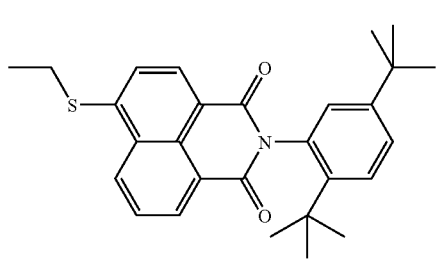

8

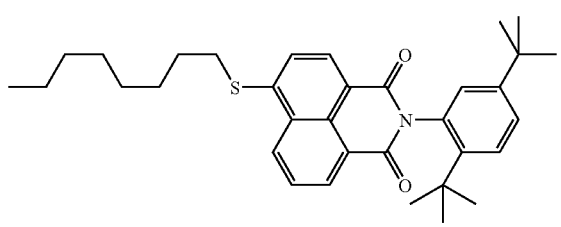

9

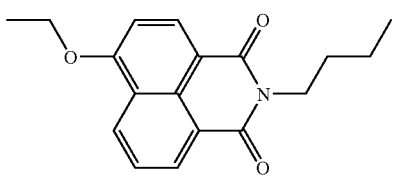

12

Preference is very particularly given, among these derivatives, to the derivative 4.

In accordance with the invention, the 1,8-naphthalimide derivative is capable of being used as scintillation agent both in a solid form, that is to say while being incorporated in a solid matrix, and in a liquid form, that is to say in solution in a solvent.

Solid matrices in which this derivative can be incorporated are in particular:
polymer matrices obtained by chain polymerization or polycondensation, in which case the polymer or the copolymer is advantageously chosen from vinyl (co) polymers (polystyrenes, poly(vinyltoluenes), poly(vinylxylenes), and the like), (co)poly(meth)-acrylates, (co)poly(meth)acrylamides, (co)poly(meth)-acrylonitriles and (co)polysiloxanes; the 1,8-naphthalimide derivative can be incorporated in the matrix either by simple dispersion or by being grafted to the chains by (co)polymerization;

matrices obtained by sol-gel technology of the type of those described by B. Kesanli et al. in *Appl. Phys. Lett.*, 2006, 89, 214104;

matrices composed of one or more hydrocarbons (saturated or unsaturated) which are solid at ambient temperature, such as, for example, eicosane or triacontane matrices; and matrices composed of a mixture of liquid crystals, such as, for example, those described by M. I. Barnik et al. in *Nucl. Instrum. Methods Phys. Res., Sect. A* 2000, 449, 537-545.

Solvents in which the 1,8-naphthalimide derivative can be dissolved are mainly aromatic organic solvents, such as, for example, xylene, benzene, toluene, mesitylene, pseudocumene or p-isopropylbiphenyl, and their mixtures, toluene being particularly preferred. Other "safe" solvents, having a high flash point (of approximately 150° C.), can also be envisaged, such as, for example, dodecylbenzene (LAB), (1-phenylethyl)xylene (PXE) or bis(1-methylethyl)-naphthalene (DIN).

However, it is also possible to use nonaromatic organic solvents, such as alcohols or ketones, or even water, mixed or not mixed with an organic solvent. However, in the latter case, it is advisable for the derivative to be provided in the form of a salt, for example an ammonium salt, by virtue of the presence of a protonated tertiary amine group carried by any one of the $R^1$ to $R^3$ radicals.

In all cases, the concentration of the 1,8-naphthalimide derivative in the solvent is advantageously at least equal to 3 g/l. This concentration, which can range up to saturation of the solvent with derivative, is preferably between 8 and 12 g/l and is ideally 10 g/l.

In accordance with the invention, the 1,8-naphthalimide derivative can be used in conjunction with one or more boron-comprising doping agents, so that it can also detect thermal neutrons. Such doping agents are, for example, o-carborane or alkyl borates, such as trimethyl borate.

Also, the 1,8-naphthalimide derivative can be used in conjunction with one or more agents capable of conferring, on the matrix or on the solvent in which it is found, better resistance to radiation. Such an agent is, for example, diphenyl oxide.

Whatever the form under which it is used and whatever the possible agents with which it is combined, the 1,8-naphthalimide derivative preferably exhibits a microanalytical degree of purity, that is to say a degree of purity of greater than or equal to 99.5%.

Another subject-matter of the invention is a liquid scintillator which comprises a 1,8-naphthalimide derivative corresponding to the formula (I) represented below:

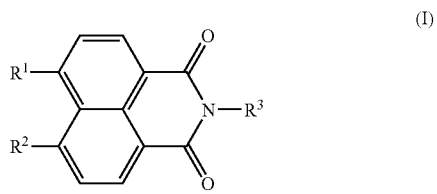

(I)

in which:
$R^1$ represents an electron-donating group;
$R^2$ represents a hydrogen atom or an electron-donating group identical to or different from $R^1$;
the electron-donating group or groups being chosen from:
—OR' and —SR' groups, where R' represents a saturated or unsaturated and linear or branched $C_1$ to $C_{20}$ hydrocarbon group which is optionally substituted, or a saturated cyclic $C_3$ to $C_{10}$ hydrocarbon group which is optionally substituted, or an aryl or heteroaryl group which is optionally substituted; and —NR'R" groups, where R' is as defined above while R" represents either a hydrogen atom, or a saturated or unsaturated and linear or branched $C_1$ to $C_{20}$ hydrocarbon group which is optionally substituted, or a saturated cyclic $C_3$ to $C_{10}$ hydrocarbon group which is optionally substituted, or an aryl or heteroaryl group which is optionally substituted;

$R^3$ represents:

an acyl group, or a saturated or unsaturated and linear or branched $C_1$ to $C_{20}$ hydrocarbon group which is optionally substituted, or a saturated cyclic $C_3$ to $C_{10}$ hydrocarbon group which is optionally substituted, or a saturated $C_3$ to $C_{10}$ heterocyclic group which is optionally substituted, or an aryl or heteroaryl group which is optionally substituted; or one of its salts, in solution in a solvent.

In this liquid scintillator, it is preferable for the 1,8-naphthalimide derivative to exhibit an emission wavelength of between 350 and 550 nm and better still between 380 and 470 nm.

Consequently, this derivative preferably corresponds to the general formula (I) in which $R^1$ represents an —OR' or —SR' group, where R' is as defined above, while $R^2$ represents a hydrogen atom.

Advantageously, $R^1$ represents a $C_1$ to $C_{20}$ and better still $C_1$ to $C_{10}$ alkoxy, alkenyloxy or alkylsulphanyl group.

Furthermore, $R^3$ preferably represents an aryl or heteroaryl group substituted in the 2 and 5 positions, with respect to the nitrogen atom of the naphthalimide ring system, by a branched $C_3$ to $C_6$ alkyl group, advantageously a di(t-butyl) phenyl group.

In the liquid scintillator, the 1,8-naphthalimide derivative is preferably chosen from the derivatives 4, 5, 6, 7, 8, 9 and 12 represented above, the derivative 4 being, here again, very particularly preferred.

Furthermore, the solvent is preferably an aromatic organic solvent of the xylene, benzene, toluene, mesitylene, pseudocumene, dodecylbenzene or p-isopropylbiphenyl type, or a mixture of such solvents, toluene being particularly preferred.

With regard to the 1,8-naphthalimide derivative, it is advantageously present at a concentration at least equal to 3 g/l and preferably of between 8 and 12 g/l, an ideal concentration being 10 g/l.

Optionally, the liquid scintillator can furthermore comprise one or more boron-comprising doping agents, for example of the type of those mentioned above, and/or one or more agents capable of conferring on it better resistance to radiation, of the type of those mentioned above.

On the other hand, and this is in particular one of the main advantages of the invention, it is not necessary to provide for the presence of another fluorescent compound in the liquid scintillator.

Among the 1,8-naphthalimide derivatives capable of being used as scintillation agents in accordance with the invention, some are known as chemical compounds while others have, to the knowledge of the Inventors, never been described.

Another subject-matter of the invention is thus a 1,8-naphthalimide derivative which corresponds to the general formula (I) represented above and in which:

$R^1$ represents an electron-donating group chosen from —OR' and —SR' groups, where R' represents a saturated or unsaturated and linear or branched $C_1$ to $C_{20}$ hydrocarbon group which is optionally substituted, or a saturated cyclic $C_3$ to $C_{10}$ hydrocarbon group which is optionally substituted, or an aryl or heteroaryl group which is optionally substituted;

$R^2$ represents a hydrogen atom or an electron-donating group which is also chosen from —OR' and —SR' groups, where R' is as defined above, while $R^3$ represents an aryl or heteroaryl group substituted in the 2 and 5 positions, with respect to the nitrogen atom of the naphthalimide ring system, by a branched $C_3$ to $C_6$ alkyl group;

and its salts.

In this derivative, it is preferable for:

$R^2$ to represent a hydrogen atom;

$R^1$ to represent a $C_1$ to $C_{20}$ and better still $C_1$ to $C_{10}$ alkoxy, alkenyloxy or alkylsulphanyl group; and $R^3$ to represent a di(t-butyl)phenyl group.

In accordance with the invention, the 1,8-naphthalimide derivative is preferably chosen from the derivatives 4, 5, 6, 7, 8 and 9 represented above, the derivative 4 being very particularly preferred.

The 1,8-naphthalimide derivatives of use as scintillation agents in accordance with the invention can be prepared by synthetic routes within the scope of a person skilled in the art.

In particular, these derivatives can be synthesized according to the general reaction scheme below:

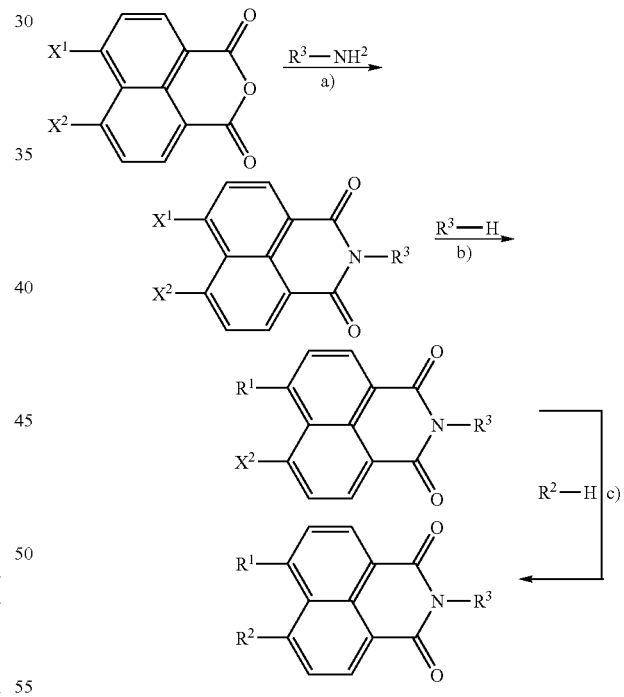

where:

$X^1$ represents a halogen atom typically a bromine atom;

$X^2$ represents a hydrogen atom if it is desired to obtain a 1,8-naphthalimide derivative of general formula (I) in which $R^2$ represents a hydrogen atom, a halogen atom identical to $X^1$ if it is desired to obtain a 1,8-naphthalimide derivative of general formula (I) in which $R^2$ represents an electron-donating group identical to $R^1$, and a nitro group if it is desired to obtain a 1,8-naphthalimide derivative of general formula (I) in which $R^2$ represents an electron-donating group different from $R^1$;

the synthesis comprises only stages a) and b) if it is desired to obtain a 1,8-naphthalimide derivative of general formula (I) in which $R^2$ represents a hydrogen atom, while it additionally comprises stage c) if it is desired to obtain a 1,8-naphthalimide derivative of general formula (I) in which $R^2$ represents an electron-donating group; stages b) and c) are carried out at the same time in the case where it is intended that $R^1$ and $R^2$ should be the same electron-donating group;

stage a) is a conventional amidation reaction by a primary amine, while stages b) and c) are nucleophilic substitution stages well known to a person skilled in the art.

If necessary, the 1,8-naphthalimide derivative thus obtained is subjected to one or more purification operations, for example purification by chromatography on silica gel, in order to obtain a microanalytical degree of purity.

Other characteristics and advantages of the invention will become apparent on reading the remainder of the description which follows, which refers to examples of the synthesis of 1,8-naphthalimide derivatives of use as scintillation agents and of the demonstration of the properties of liquid scintillators prepared from these derivatives.

Of course, these examples are given only by way of illustration of the invention and do not under any circumstances constitute a limitation thereof.

DETAILED ACCOUNT OF SPECIFIC EMBODIMENTS

Example 1

Figure 1:
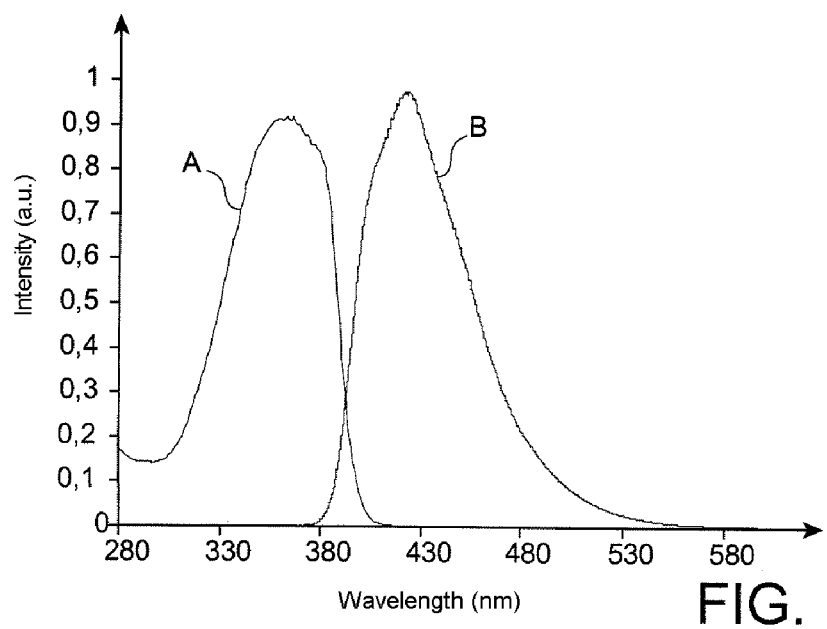
FIG. 1 illustrates the absorption spectrum (curve A) and emission spectrum (curve B) of a 1,8-naphthalimide derivative of use as scintillation agent.
Figure 2:
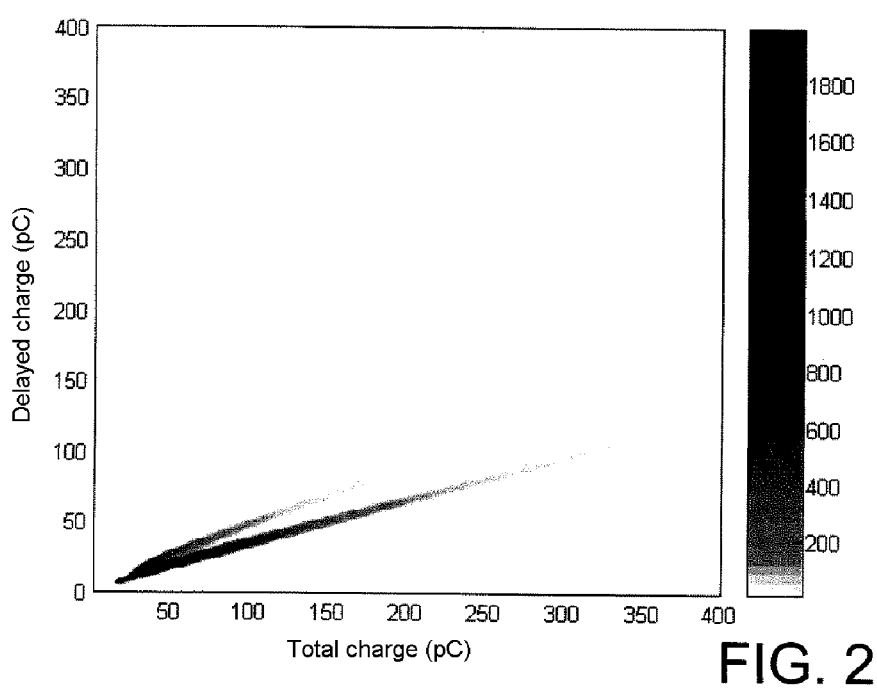
FIG. 2 illustrates the n/γ discrimination as obtained with a liquid scintillator according to the invention saturated with argon.
Figure 3:
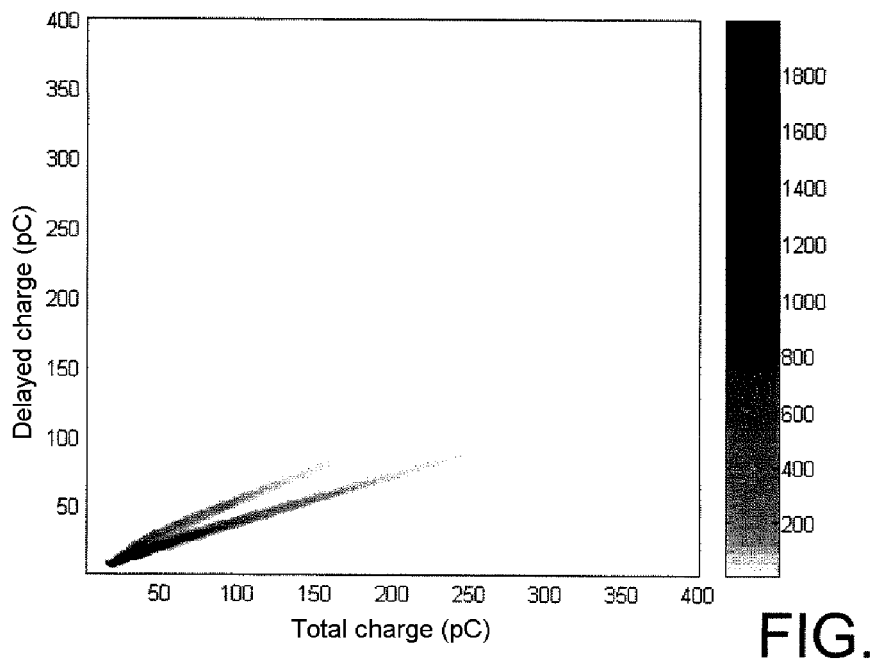
FIG. 3 illustrates the n/γ discrimination as obtained with a liquid scintillator according to the invention saturated with oxygen.
Figure 4:
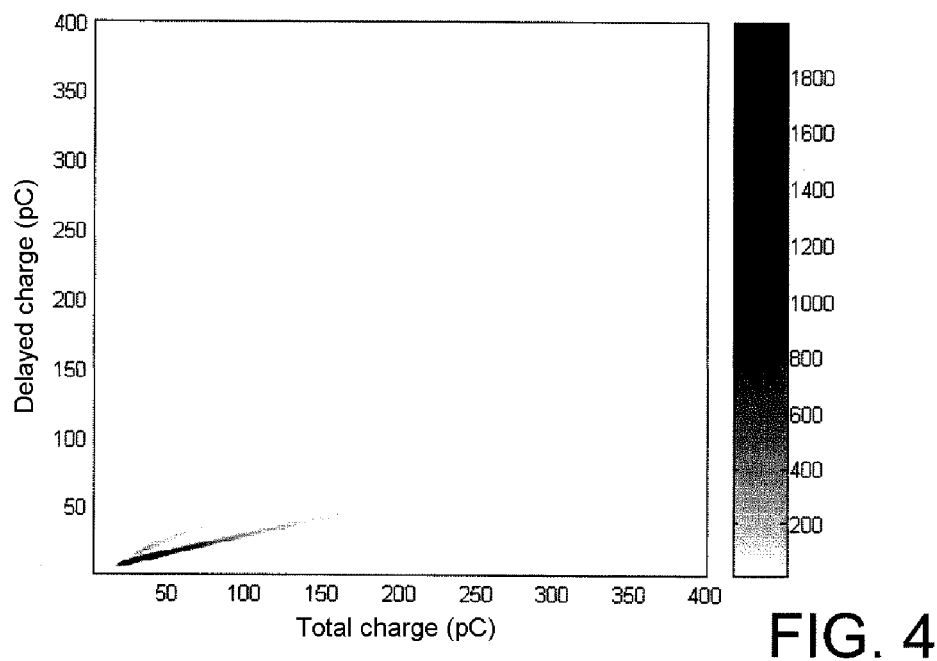
FIG. 4 illustrates the n/γ discrimination as obtained with a first commercial organic liquid scintillator, NE213, saturated with argon.
Figure 5:
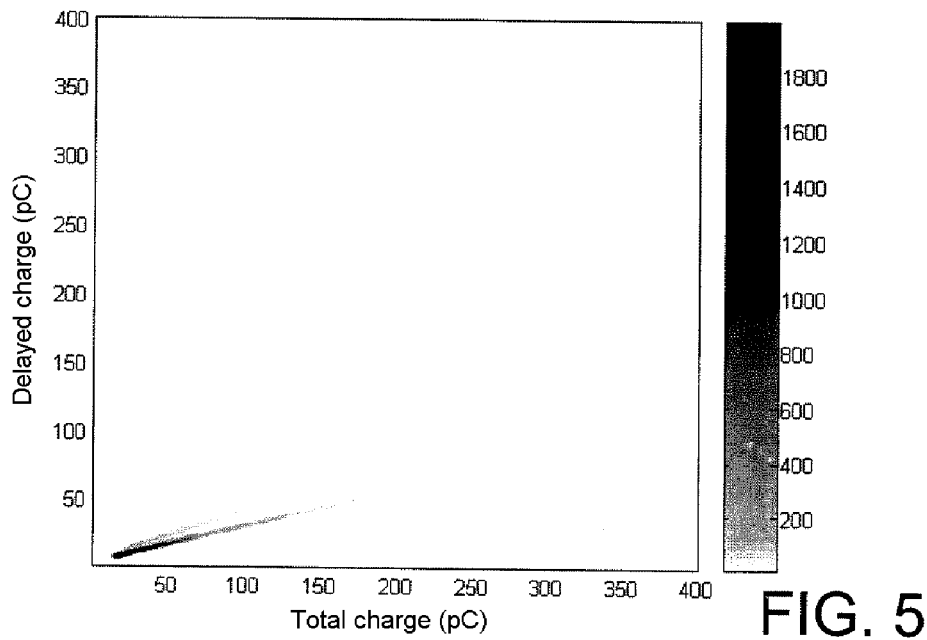
FIG. 5 illustrates the n/γ discrimination as obtained with NE213 saturated with oxygen.
Figure 6:
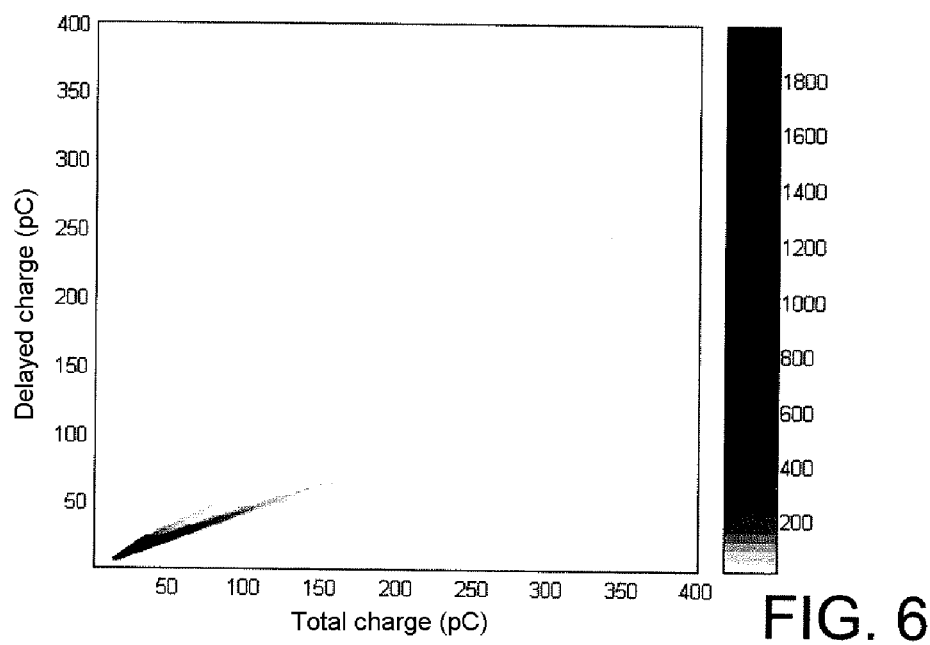
FIG. 6 illustrates the n/γ discrimination as obtained with another commercial organic liquid scintillator, Ultima Gold® AB, saturated with argon.
Figure 7:
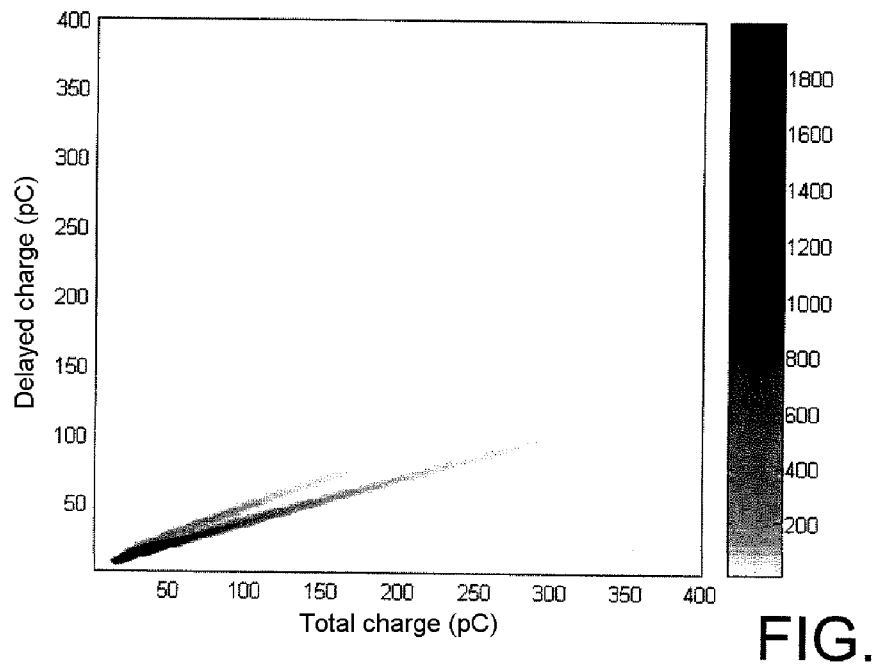
FIG. 7 illustrates the n/γ discrimination as obtained with Ultima Gold® AB saturated with oxygen.
Figure 8:
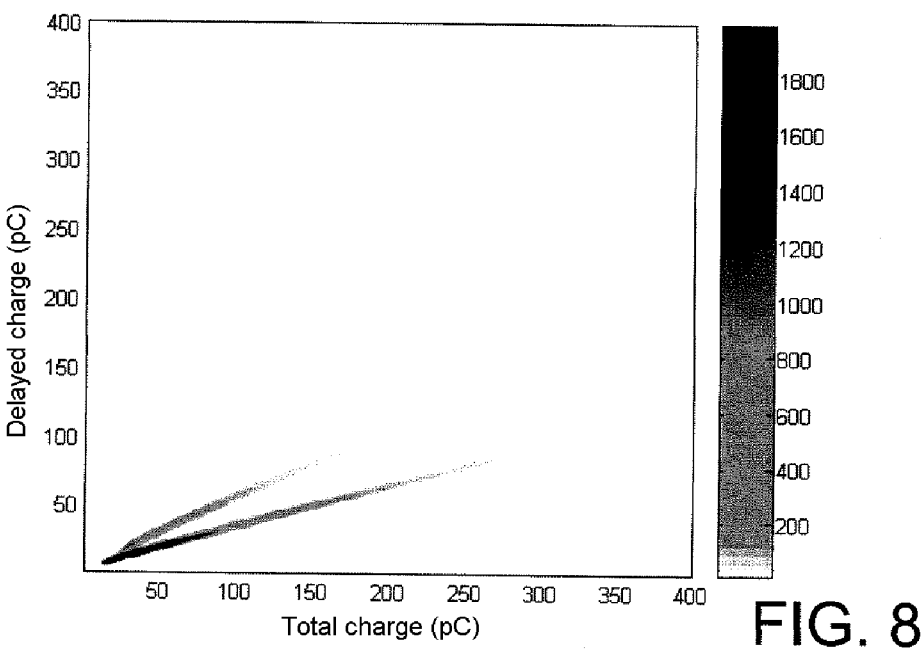
FIG. 8 illustrates the n/γ discrimination as obtained with yet another commercial organic liquid scintillator, BC-501A, saturated with argon.
Figure 9:
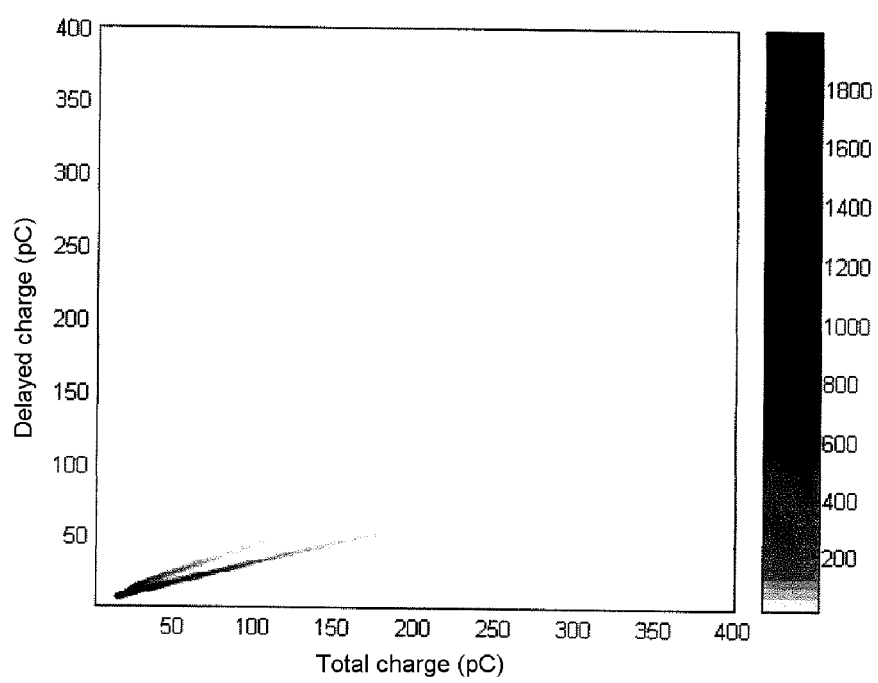
FIG. 9 illustrates the n/γ discrimination as obtained with BC-501A saturated with oxygen.

Synthesis of 1,8-naphthalimide derivatives useful as scintillation agents 1.1. N-(2',5'-di(t-butyl)phenyl)-4-ethoxy-1,8-naphthalimide The title compound, which corresponds to the derivative 4 represented above, is synthesized starting from 4-bromonaphthalic anhydride or compound 1 and from 2,5-di(t-butyl)aniline or compound 2, according to the following reaction scheme:

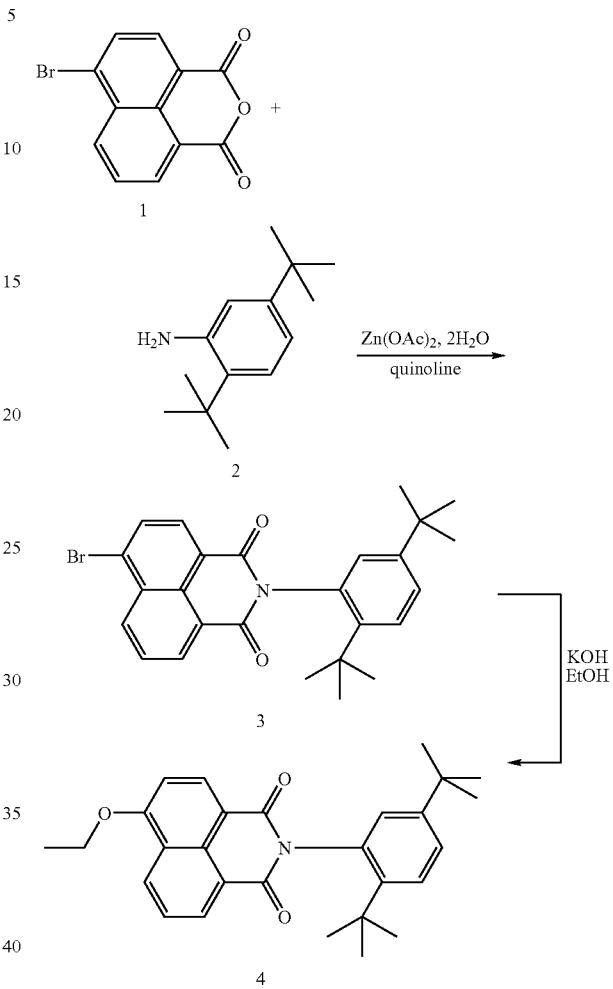

Compounds 1 and 2 are available commercially.

Synthesis of N-(2',5'-di(t-butyl)phenyl)-4-bromo-1,8-naphthalimide or compound 3

2.934 g (10.06 mmol) of compound 1 and 4.131 g (20.12 mmol) of compound 2 are covered with 100 ml of freshly distilled quinoline in a 250 ml round-bottomed flask equipped with a water-cooled reflux condenser. 773 mg (3.52 mmol) of zinc acetate dihydrate are then added and the reaction mixture is heated at reflux of the solvent for 5 hours. After returning to ambient temperature, the mixture is poured into an aqueous solution of pH=1. The aqueous phase is extracted with dichloromethane. The organic phase is dried, filtered and then concentrated. The residue is finely chromatographed on silica gel to give 4.583 g of a beige solid (Yd: 93%).

Melting point: 214° C. (dec., heptane)

$^1$H NMR (250 MHz, CDCl$_3$) δ ppm: 1.19 (s, 9H, CH$_3$); 1.23 (s, 9H, CH$_3$); 6.91 (d, 1H, J=2.2, H$_6$); 7.37 (dd, 1H, J=8.7, J=2.2, H$_4$); 7.48-7.52 (m, 1H, H$_{3'}$); 7.80 (dd, 1H, J=8.5, J=7.2, H$_6$); 7.99 (d, 1H, J=8.0); 8.38 (d, 1H, J=8.1); 8.55 (dd, 1H, J=8.5, J=1.3); 8.64 (dd, 1H, J=7.2, J=1.3)

$^{13}$C NMR (62.9 MHz) δ ppm: 31.2, 31.7, 34.2, 35.4, 122.6, 123.5, 126.3, 127.6, 128.1, 128.7, 129.4, 130.5, 130.8, 131.1, 131.6, 132.4, 132.5, 133.5, 143.7, 150.1, 164.52, 164.57

Infrared (neat, cm$^{-1}$): 2960, 2873, 1666, 1589, 1496, 1357, 1234.

Synthesis of Derivative 4

1 g (2.15 mmol) of compound 3 and 0.154 g (2.36 mmol) of potassium hydroxide are dissolved in 10 ml of ethanol in a 25 ml round-bottomed flask. The solution is heated at 80° C. at reflux for 5 hours. After returning to ambient temperature, the solvent is evaporated, the residue is directly purified by chromatography on silica gel and then the solid is recrystallized from acetonitrile to give 775 mg of derivative 4 in the form of a white solid (Yd: 84%).

The absorption and emission spectra of this derivative are illustrated in FIG. 1, curve A corresponding to the absorption spectrum and curve B corresponding to the emission spectrum.

Melting point: 196° C. (acetonitrile)

$^1$H NMR (250 MHz, CDCl$_3$) δ ppm: 1.27 (s, 9H, CH$_3$); 1.31 (s, 9H, CH$_3$); 1.63 (t, 3H, $^3$J=6.9, CH$_3$); 4.38 (qd, 2H, $^3$J=7.0, CH$_2$—O); 6.99 (d, 1H, J=2.1, H$_{6'}$); 7.06 (d, 1H, J=8.3); 7.43 (dd, 1H, J=8.5, J=2.1); 7.57 (d, 1H, J=8.5); 7.73 (t, 1H, J=7.9); 8.58-8.67 (m, 3H)

$^{13}$C NMR (62.9 MHz, CDCl$_3$) δ ppm: 14.6, 30.3, 31.7, 34.2, 35.5, 64.8, 105.8, 115.2, 122.8, 123.8, 125.9, 126.0, 127.9, 128.6, 129.0, 129.9, 131.9, 133.2, 133.9, 143.8, 149.9, 160.4, 165.0, 165.6

Infrared (neat, cm$^{-1}$): 2964, 2873, 1704, 1664, 1589, 1353, 1238

Elemental analysis: calculated (found) for C$_{28}$H$_{31}$NO$_3$.0.5H$_2$O:
C: 76.68% (77.1%)
H: 7.35% (7.3%)
N: 3.19% (3.7%)

1.2. N-(2',5'-di(t-butyl)phenyl)-4-methoxy-1,8-naphthalimide

The title compound, which corresponds to derivative 5 represented above, is synthesized according to a protocol identical to that described above for the synthesis of derivative 4, apart from the fact that the reaction between compound 3 and the potassium hydroxide takes place in methanol at reflux at 70° C. for 5 hours. After purification by chromatography on silica gel followed by recrystallization from acetone, 166 of derivative 5 are obtained in the form of a white solid (Yd: 62%).

Melting point: 230° C. (acetone)

$^1$H NMR (250 MHz, CDCl$_3$) δ ppm: 1.27 (s, 9H, CH$_3$); 1.31 (s, 9H, CH$_3$); 4.15 (s, 3H, CH$_3$—O); 6.99 (d, 1H, J=2.2, H$_{6'}$); 7.08 (d, 1H, J=8.3); 7.43 (dd, 1H, J=8.5, J=2.2); 7.57 (d, 1H, J=8.5); 7.74 (t, 1H, J=7.6); 8.60-8.67 (m, 3H)

$^{13}$C NMR (62.9 MHz, CDCl$_3$) δ ppm: 31.2, 31.7, 34.2, 35.5, 56.3, 105.2, 115.5, 122.8, 123.8, 126.0, 126.1, 127.8, 128.6, 128.9, 129.8, 132.0, 133.1, 133.9, 143.8, 149.9, 161.0, 164.9, 165.5

Infrared (neat, cm$^{-1}$): 2960, 2869, 1700, 1666, 1591, 1355, 1236

Elemental analysis: calculated (found) for C$_{27}$H$_{29}$NO$_3$.0.5H$_2$O.
C: 76.39% (76.7%)
H: 7.12% (7.4%)
N: 3.30% (3.6%).

1.3. N-(2',5'-di(t-butyl)phenyl)-4-allyloxy-1,8-naphthalimide

The title compound, which corresponds to derivative 6 represented above, is synthesized according to a protocol identical to that described above for the synthesis of derivative 4, apart from the fact that the reaction between compound 3 and the potassium hydroxide takes place in allyl alcohol at 70° C. for 16 hours. 344 mg of compound 6 are thus obtained in the form of a pale yellow solid (Yd: 72%).

Melting point: 183-184° C.

$^1$H NMR (400 MHz) δ ppm: 1.27 (s, 9H, CH$_3$); 1.30 (s, 9H, CH$_3$); 4.87-4.89 (m, 2H, CH$_2$—O); 5.43 (dd, 1H, J$^{cis}$=10.4, J$^{gem}$=1.4, CH$_2$=C); 5.56 (dd, 1H, J$^{trans}$=17.6, J$^{gem}$=1.4, CH$_2$=C); 6.15-6.23 (m, 1H, CH=C); 6.98 (d, 1H, J=2.0, H$_{6'}$); 7.07 (d, 1H, J=8.4); 7.42 (dd, 1H, J=8.8, J=2.4); 7.56 (d, 1H, J=8.8); 7.74 (dd, 1H, J=8.4, J=7.6); 8.59 (d, 1H, J=8.4); 8.64-8.68 (m, 2H)

$^{13}$C NMR (100.6 MHz, CDCl$_3$) δ ppm: 31.6, 32.1, 34.6, 35.9, 70.1, 106.7, 116.0, 119.2, 123.3, 124.3, 126.4, 126.5, 128.3, 129.0, 129.4, 130.3, 132.3, 132.4, 133.5, 134.2, 144.2, 150.3, 160.3, 165.3, 165.9

Infrared (neat, cm$^{-1}$): 2962, 2873, 1702, 1662, 1589, 1355, 1234

Elemental analysis: calculated (found) for C$_{29}$H$_{31}$NO$_3$:
C: 78.88% (78.9%)
H: 7.08% (7.1%)
N: 3.17% (3.6%)

1.4. N-(2',5'-di(t-butyl)phenyl)-4-octyloxy-1,8-naphthalimide

The title compound, which corresponds to derivative 7 represented above, is synthesized according to a protocol identical to that described above for the synthesis of derivative 4, apart from the fact that the reaction between compound 3 and the potassium hydroxide takes place in octanol at 70° C. for 16 hours. 214 mg of derivative 7 are thus obtained in the form of a pale yellow solid (Yd: 29%).

$^1$H NMR (250 MHz, CDCl$_3$) δ ppm: 0.88 (t, 3H, J=6.0, CH$_3$); 1.27 (s, 9H, CH$_3$); 1.30 (s, 9H, CH$_3$) 1.30-1.70 (m, 10H); 2.00 (qt, 2H, J=6.8, CH$_2$); 4.30 (t, 2H, J=6.3, CH$_2$); 6.99 (d, 1H, J=2.1, H$_{6'}$); 7.06 (d, 1H, J=8.3); 7.40-7.47 (m, 1H); 7.54-7.59 (m, 1H); 7.74 (t, 1H, J=8.1, H$_6$); 8.57-8.67 (m, 3H)

$^{13}$C NMR (62.9 MHz, CDCl$_3$) δ ppm: 14.1, 22.7, 26.1, 29.0, 29.2, 29.3, 31.2, 31.7, 31.8, 34.2, 35.5, 69.1, 105.9, 115.2, 122.8, 123.8, 125.9, 127.9, 128.6, 131.2, 131.6, 131.9, 132.5, 133.2, 133.9, 143.8, 149.9, 160.6, 164.9, 165.5.

1.5. N-=(2',5'-di(t-butyl)phenyl)-4-ethylsulphanyl-1,8-naphthalimide

The title compound, which corresponds to derivative 8 represented above, is synthesized according to a protocol identical to that described above for the synthesis of derivative 4, apart from the fact that the reaction between compound 3 and the potassium hydroxide takes place in ethanethiol at reflux at 60° C. for 5 hours. 460 mg of derivative 8 are thus obtained in the form of a yellow solid (Yd: 66%).

$^1$H NMR (250 MHz, CDCl$_3$) δ ppm: 1.19 (s, 9H, CH$_3$); 1.23 (s, 9H, CH$_3$); 1.41 (t, 3H, J=7.4, CH$_3$); 3.13 (qd, 2H, J=7.4, CH$_2$); 6.90 (d, 1H, J=2.0, H$_{6'}$); 7.33-7.38 (m, 1H); 7.46-7.51 (m, 2H); 7.69 (t, 1H, J=7.5, H$_6$); 8.44 (d, 1H, J=7.9); 8.50-8.60 (m, 2H)

$^{13}$C NMR (62.9 MHz, CDCl$_3$) δ ppm: 13.6, 26.4, 31.2, 31.7, 33.9, 35.5, 115.0, 115.7, 119.5, 122.7, 123.6, 126.1, 126.6, 127.8, 128.7, 129.7, 130.3, 131.2, 132.9, 143.8, 145.5, 150.0, 165.03, 165.05.

1.6. N-(2',5'-di(t-butyl)phenyl)-4-octylsulphanyl-1,8-naphthalimide

The title compound, which corresponds to derivative 9 represented above, is synthesized according to a protocol identical to that described above for the synthesis of derivative 4, apart from the fact that the reaction between compound 3 and the potassium hydroxide takes place in octanethiol at reflux at 60° C. for 16 hours. 887 mg of derivative 9 are thus obtained in the form of a yellow solid (Yd: 81%).

$^1$H NMR (250 MHz, CDCl$_3$) δ ppm: 0.81 (t, 3H, J=6.9, CH$_3$); 1.20 (s, 9H, CH$_3$); 1.20-1.56 (m, 10H); 1.24 (s, 9H, CH$_3$); 1.76 (qt, 1H, J=7.6, CH$_2$); 3.11 (t, 2H, J=7.4, CH$_2$); 6.91 (d, 1H, J=2.2, H$_6$·); 7.36 (dd, 1H, J=8.5, J=2.2); 7.48-7.52 (m, 2H); 7.70 (t, 1H, J=8.4, H$_6$); 8.45 (d, 1H, J=7.9); 8.54-8.61 (m, 2H)

$^{13}$C NMR (62.9 MHz, CDCl$_3$) δ ppm: 14.1, 22.6, 28.4, 29.0, 29.7, 31.2, 31.3, 31.7, 31.8, 32.3, 34.2, 35.5, 115.0, 115.7, 119.4, 122.6, 123.6, 126.1, 126.6, 127.8, 128.7, 129.8, 130.3, 131.1, 132.9, 143.8, 145.9, 149.9, 165.03, 165.05.

1.7. N-butyl-4-ethoxy-1,8-naphthalimide

The title compound, which corresponds to derivative 12 represented above, is synthesized starting from compound 1 and from n-butylamine or compound 10, according to the following reaction scheme:

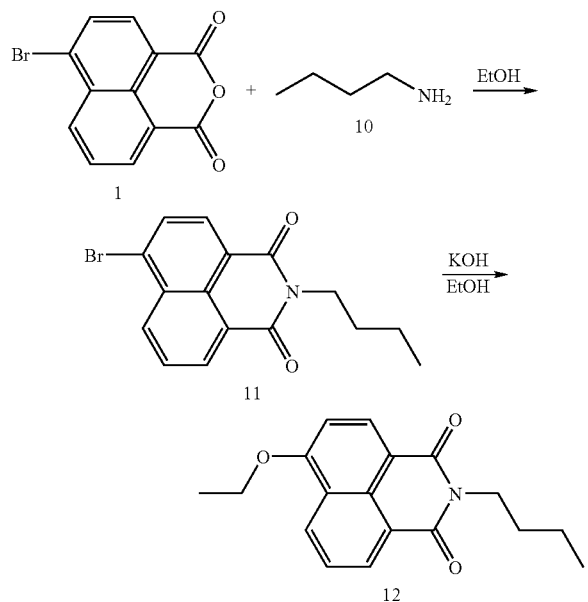

Synthesis of N-butyl-4-bromo-1,8-naphthalimide or compound 11

399 mg (1.44 mmol) of compound 1 are dissolved in 20 ml of ethanol in a 100 ml round-bottomed flask. 154 µl (1.55 mmol) of compound 10 are then added and the solution is heated to 80° C. for 8 hours. After returning to ambient temperature, the precipitate formed is filtered off and then washed twice with water. It is dried and then recrystallized from ethanol under hot conditions. Compound 11 is thus isolated in the form of yellow flakes (336 mg, Yd: 72%).

Synthesis of Derivative 12

332 mg (1.0 mmol) of compound 11 and 97.8 mg (1.5 mmol) of potassium hydroxide are covered with absolute ethanol in a 25 ml round-bottomed flask. The mixture is heated at 80° C. for 16 hours. After returning to ambient temperature, the solvent is evaporated and the residue is subjected directly to column chromatography on silica gel. 115 mg of derivative 12 are thus obtained in the form of a light yellow solid (Yd: 39%).

The results of the analyses for characterization of this compound are in accordance with those described in the literature.

Example 2

Properties of the Liquid Scintillators According to the Invention 2.1. Physical Properties The performances of six liquid scintillators according to the invention were tested and compared with those of four commercial organic liquid scintillators.

The liquid scintillators according to the invention are composed of derivative 4 in solution at 10 g/l in m-xylene, toluene, mesitylene, benzene, p-xylene and p-isopropylbiphenyl respectively, while the commercial organic liquid scintillators are (1) a mixture of p-terphenyl and POPOP (1,4-di(5-phenyloxazol-2-yl)benzene) in a ratio of 4 at 0.1 g/l in toluene; (2) NE 213; (3) Ultima Gold® AB from PerkinElmer and (4) BC-501A from Bicron.

The instrumentation used is that described by S. Normand et al. in *Nucl. Instrum. Methods Phys. Res. A* 2002, 484, 342-350. It is n/γ discrimination by comparison of charges which is selected.

The photomultiplier is a Photonis XP2020 model which operates at a voltage of 2 kV.

The liquid scintillators are positioned in a 38×10×10 mm$^3$ cell, all the walls of which, with the exception of that which is pressed against the photomultiplier, are covered with a titanium oxide paint.

For all the tests, the electronic editing line is the same with constant adjustments. The voltage of the photomultiplier is also kept constant, with a constant amplification factor, and the distribution between slow window and fast window is itself also constant.

Two different sources of radiation were used: a cobalt-60 source of 48 kBq (which emits only gamma radiation), in order to measure the light intensity produced by the scintillators and the rise time and the decay time of the pulses, and a californium-252 source of 74 MBq (which emits neutrons and gamma radiation), in order to determine the figure of merit M (FOM), which represents the ability of a liquid scintillator to separate the lobe of the neutrons from that of the gamma radiation, and the angle θ which is formed between these lobes.

The figure of merit M was calculated by a method improved from that described by M. Moszyński et al. in *Nucl. Instrum. Methods Phys. Res. A* 1994, 350, 226-234, from the equation:

$$\frac{\text{Separation of the peaks}}{(FWHM_\gamma + FWHM_n)}$$

in which FWHM represents the full width at half maximum of the lobes.

All the liquid scintillators were subjected to bubbling with argon for at least ten minutes.

The results are recorded in Table 1 below.

This table shows that the liquid scintillators according to the invention exhibit spectroscopic properties which are broadly as advantageous as those of commercial organic liquid scintillators.

TABLE 1

| Liquid scintillator | Light intensity[a] | Rise time (ns)[b] | Decay time (ns)[b] | FOM[c] | θ[d] |
|---|---|---|---|---|---|
| p-terephenyl/POPOP (4/0.1 g/l) in toluene | 100 | 2.46 | 7.29 | 0.6-1.9 (40-280) | 5.0 |
| NE213 | 85 | 2.77 | 9.05 | 0.8-1.8 (35-200) | 7.8 |
| Ultima Gold®AB | 77 | 2.55 | 9.90 | 0.7-1.3 (40-135) | 6.3 |
| BC-501A | 64 | 2.73 | 8.61 | 1.0-2.4 (35-250) | 8.3 |
| Derivative 4 at 10 g/l in m-xylene | 64 | 2.93 | 14.86 | 0.6-1.6 (40-260) | 5.0 |
| Derivative 4 at 10 g/l in toluene | 59 | 2.96 | 14.92 | 0.6-1.6 (35-270) | 5.1 |
| Derivative 4 at 10 g/l in mesitylene | 56 | 3.02 | 13.82 | 0.4-1.2 (45-200) | 3.5 |
| Derivative 4 at 10 g/l in benzene | 51 | 3.06 | 15.24 | 0.3-1.4 (50-200) | 7.0 |
| Derivative 4 at 10 g/l in p-xylene | 50 | 3.01 | 15.25 | 0.6-1.4 (40-210) | 4.8 |
| Derivative 4 at 10 g/l in p-isopropylbiphenyl | 33 | 3.45 | 13.16 | 0.5-0.9 (45-200) | 3.1 |

[a] relative to 100 for the reference scintillator (POPOP)
[b] taken within 20 and 80% of the part of the pusle concerned
[c] calculated from the equation $\frac{\text{Separation of the peaks}}{(\text{FWHM}_y + \text{FWHM}_n)}$,
where FWHM represents the full width at half maximum of the lobes; the measurement range over which the FOM was determined is shown in brackets.
[d] angle in degrees formed between the lobe of the neutrons and that of the gamma radiation.

Furthermore, the ability of liquid scintillators according to the invention, prepared from a 1,8-naphthalimide derivative other than derivative 4, to discriminate between fast neutrons and gamma rays was also tested using instrumentation and operating conditions identical to those described above.

These liquid scintillators are respectively composed of derivative 5, derivative 8, derivative 9 and derivative 12 in solution at 10 g/l in toluene.

The figure of merit M (FOM) and the angle θ formed between the lobe of the neutrons and that of the gamma radiation which are obtained for each of the liquid scintillators tested are presented in Table 2 below.

TABLE 2

| Liquid scintillator | FOM[c] | θ[d] |
|---|---|---|
| Derivative 5 at 10 g/l in toluene | 0.4-1.1 (35-150) | 5.5 |
| Derivative 6 at 10 g/l in toluene | n.d. | n.d. |
| Derivative 7 at 10 g/l in toluene | n.d. | n.d. |
| Derivative 8 at 10 g/l in toluene | 0.3-1.2 (40-180) | 4.7 |
| Derivative 9 at 10 g/l in toluene | 0.4-1.0 (64-150) | 6.7 |
| Derivative 12 at 10 g/l in toluene | 0.2-0.8 (40-180) | 3.6 |

[c] calculated from the equation $\frac{\text{Separation of the peaks}}{(\text{FWHM}_y + \text{FWHM}_n)}$,
where FWHM represents the full width at half maximum of the lobes; the measurement range over which the FOM was determined is shown in brackets;
[d] angle in degrees formed between the lobe of the neutrons and that of the gamma radiation;
n.d.: not determined due to an excessively low value.

2.2. Insensitivity to Dissolved Oxygen

The sensitivity to dissolved oxygen of a liquid scintillator according to the invention, composed of derivative 4 in solution at 10 g/l in toluene, was tested and compared with that of the liquid scintillators NE213, BC-501A and Ultima Gold® AB.

In order to do this, the ability to discriminate between fast neutrons and gamma rays was tested for each liquid scintillator after saturation with argon and after saturation with oxygen, using instrumentation and operating conditions identical to those described above.

The figure of merit M (FOM), the mean of the figure of merit M taken from the values of total charge between 50 and 100 pC (<FOM>) and the angle θ formed between the lobe of the neutrons and that of the gamma radiation which are obtained for each of the liquid scintillators tested are presented in Table 3 below.

TABLE 3

| Liquid scintillator | FOM | <FOM> | θ |
|---|---|---|---|
| Derivative 4 at 10 g/l in toluene saturated with argon | 0.6-1.6 (35-270) | 0.93 | 5.1 |
| NE213 saturated with argon | 0.8-1.8 (35-200) | 1.39 | 7.8 |
| BC-501A saturated with argon | 1.0-2.4 (35-250) | 1.66 | 8.3 |
| Ultima Gold AB saturated with argon | 0.7-1.3 (40-135) | 0.91 | 6.3 |
| Derivative 4 at 10 g/l in toluene saturated with $O_2$ | 0.5-1.8 (35-250) | 1.00 | 5.5 |
| NE213 saturated with $O_2$ | 0.3-1.5 (35-220) | 0.97 | 4.1 |
| BC-501A saturated with $O_2$ | 0.3-1.8 (35-240) | 1.12 | 4.1 |
| Ultima Gold AB saturated with $O_2$ | 0.3-1.2 (40-200) | 0.73 | 4.4 |

The n/γ discrimination as obtained, after saturation with argon and saturation with oxygen, for the various liquid scintillators tested is illustrated in FIGS. 2 to 9.

Table 3 and these figures show that the liquid scintillator according to the invention retains its performance in terms of n/γ discrimination when it is saturated with oxygen, in contrast to commercial organic liquid scintillators, for which it is possible in particular to observe that the angle θ formed between the lobe of the neutrons and that of the gamma radiation decreases by a factor of approximately 2 after saturation with oxygen.

Furthermore, tests have made it possible to confirm that the liquid scintillator according to the invention does not require any specific precautions for the packaging and storage thereof. It can thus be kept under an atmosphere of air and in daylight without its properties of discrimination being affected, even after several months.

The invention claimed is:

1. A liquid scintillator comprising a 1,8-naphthalimide derivative of formula (I):

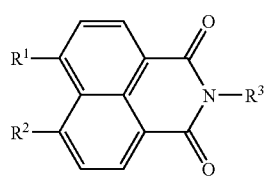
(I)

wherein the 1,8-naphthalimide derivative is selected from the group consisting of 1,8-naphthalimide derivatives having the formulas:

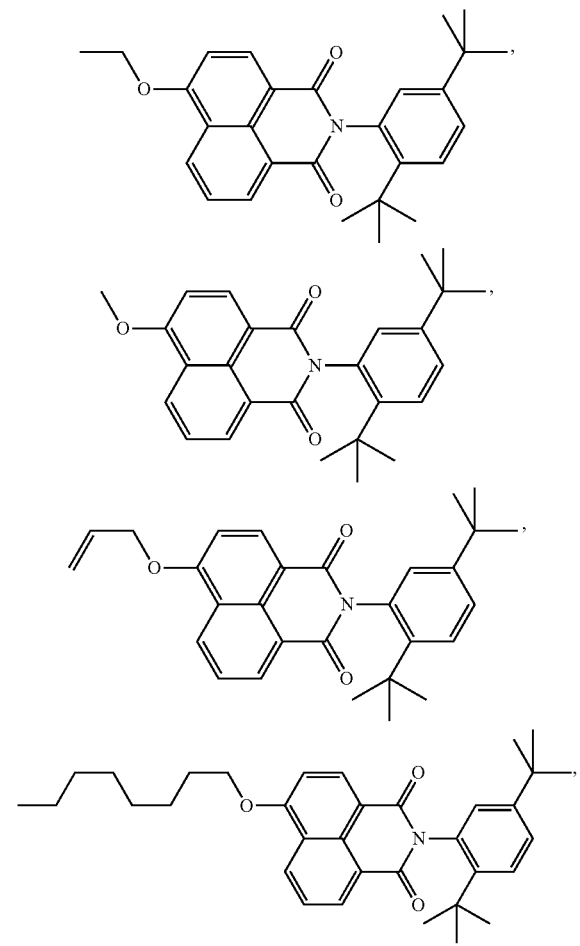

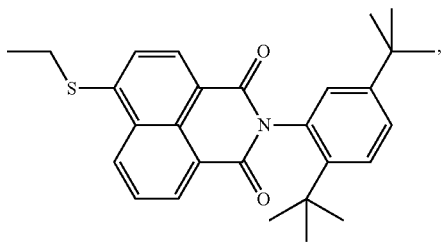 [SMILES: CCOc1ccc2c3c(cccc13)C(=O)N(c1cc(C(C)(C)C)ccc1C(C)(C)C)C2=O]

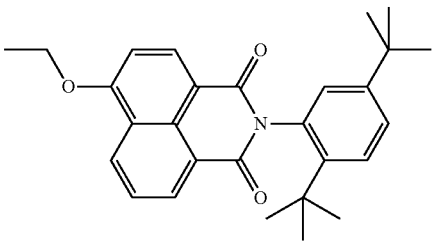

and salts thereof;

wherein said 1,8-naphthalimide derivative or salt thereof is in solution in a solvent.

2. The liquid scintillator of claim 1, wherein the 1,8-naphthalimide derivative exhibits an emission wavelength of about 350 to about 550 nm.

3. The liquid scintillator of claim 1, wherein the 1,8-naphthalimide derivative is represented by the following formula:

4. The liquid scintillator of claim 1, wherein the solvent is an aromatic organic solvent or a mixture of aromatic organic solvents.

5. The liquid scintillator of claim 4, wherein the solvent is toluene.

6. The liquid scintillator of claim 1, wherein the solution comprises at least three grams of the 1,8-naphthalimide derivative per liter of solution.

7. The liquid scintillator of claim 1, further comprising at least one boron-comprising doping agent.

8. A 1,8-Naphthalimide derivative comprising formula (I):

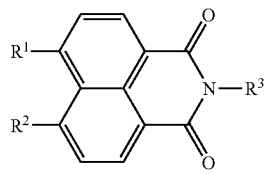

wherein the 1,8-naphthalimide derivative is selected from the group consisting of 1,8-naphthalimide derivatives having the formulas:

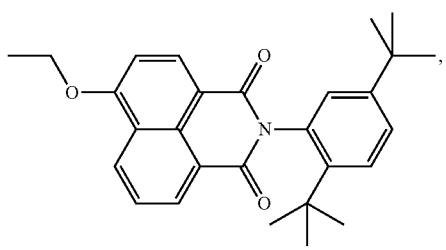

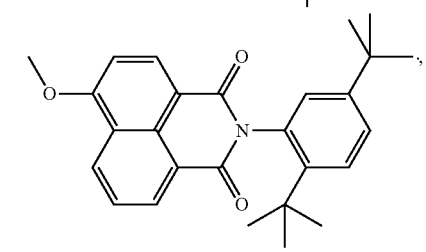

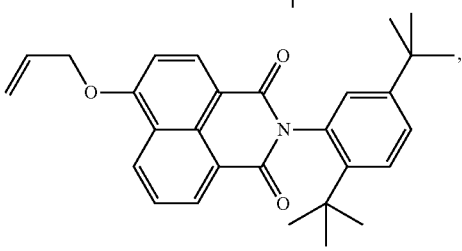

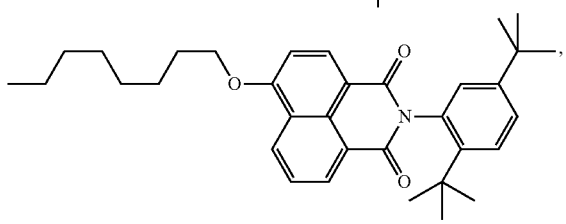

-continued

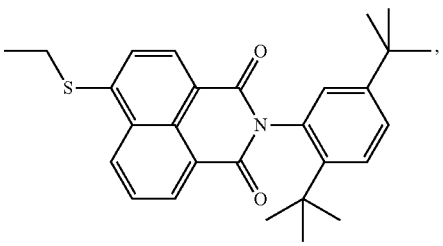 [SMILES: CCOc1ccc2c3c(cccc13)C(=O)N(c1cc(C(C)(C)C)ccc1C(C)(C)C)C2=O]

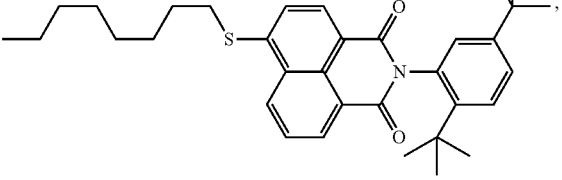

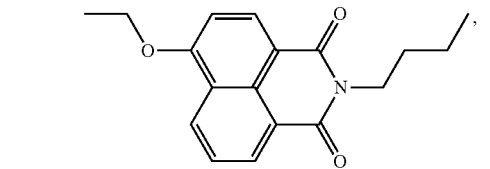

and salts thereof.

9. A 1,8-Naphthalimide derivative according to claim 8, comprising the formula:

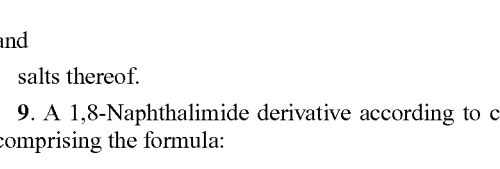

10. The liquid scintillator of claim 1, wherein the 1,8-naphthalimide derivative exhibits an emission wavelength between about 380 to about 470 nm.

11. The liquid scintillator of claim 1, wherein the solution comprises between 8 and 12 grams of the 1,8-naphthalimide derivative per liter of solution.

* * * * *